(12) United States Patent
Kobilka et al.

(10) Patent No.: US 10,106,564 B2
(45) Date of Patent: Oct. 23, 2018

(54) FURAN-CONTAINING FLAME RETARDANT MOLECULES

(71) Applicant: International Business Machines Corporation, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/375,362

(22) Filed: Dec. 12, 2016

(65) Prior Publication Data

US 2018/0162888 A1  Jun. 14, 2018

(51) Int. Cl.
  *C07F 9/655*  (2006.01)
(52) U.S. Cl.
  CPC ................................. *C07F 9/65515* (2013.01)
(58) Field of Classification Search
  CPC .................................................. C07F 9/65515
  See application file for complete search history.

(56) References Cited

U.S. PATENT DOCUMENTS

| | | | |
|---|---|---|---|
| 8,680,183 B2 | 3/2014 | Schambony et al. |
| 8,779,040 B2 | 7/2014 | van der Weele et al. |
| 8,781,278 B2 | 7/2014 | Karayianni |
| 8,859,788 B2 | 10/2014 | Partin et al. |
| 9,145,379 B2 | 9/2015 | Graß et al. |
| 9,238,609 B2 | 1/2016 | Asthana et al. |
| 9,284,414 B2 | 3/2016 | Boday et al. |
| 9,309,407 B2 | 4/2016 | Rosenquist |
| 9,822,208 B1 | 11/2017 | Kobilka et al. |
| 2012/0252911 A1 | 10/2012 | Fleckenstein et al. |
| 2012/0322968 A1 | 12/2012 | Matsuda et al. |
| 2013/0171397 A1 | 7/2013 | Ghosh et al. |
| 2015/0001213 A1 | 1/2015 | Nederberg et al. |
| 2015/0267095 A1 | 9/2015 | Parker et al. |
| 2016/0017089 A1 | 1/2016 | Stephen et al. |

FOREIGN PATENT DOCUMENTS

| | | |
|---|---|---|
| CN | 104262905 A | 1/2015 |
| GB | 2499491 B | 7/2016 |
| WO | WO-2015095466 A2 | 6/2015 |

OTHER PUBLICATIONS

Petrov et al., 32 Zhurnal Obshchei Khimii 3716-20 (1962), (Year: 1962).*
Appendix P, List of IBM Patent or Applications Treated as Related, Mar. 22, 2017, 2 pages.
Lauzon, "Cheaper route for polyester raw material at pilot plant stage", plasticnews.com (online), Jan. 27, 2016, 2 pages, URL: http://www.plasticsnews.com/article/20160127/NEWS/160129818.
Kandola et al., "Flame Retardance and Physical Properties of Novel Cured Blends of Unsaturated Polyester and Furan Resins", Polymers, Feb. 2015, vol. 7, Issue 2, pp. 298-315, Multidisciplinary Digital Publishing Institute (MDPI.com) online, DOI: doi:10.3390/polym7020298, URL: http://www.mdpi.com/2073-4360/7/2/298.
U.S. Appl. No. 15/375,519, to Brandon M. Kobilka et al., entitled, *Cross-Linkable Flame Retardant Materials*, assigned to International Business Machines Corporation, 44 pages, filed Dec. 12, 2016.

* cited by examiner

*Primary Examiner* — Timothy R Rozof
(74) *Attorney, Agent, or Firm* — Roy R. Salvagio; Robert R. Williams; Kennedy Lenart Spraggins LLP

(57) ABSTRACT

A furan-containing flame retardant molecule includes a furan moiety bonded to a phosphorus moiety via a phosphoryl linkage or via a phosphinyl linkage.

11 Claims, 13 Drawing Sheets

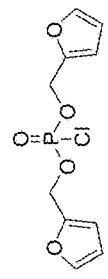 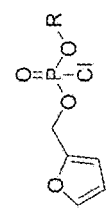 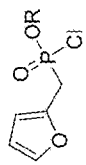
FIG. 1

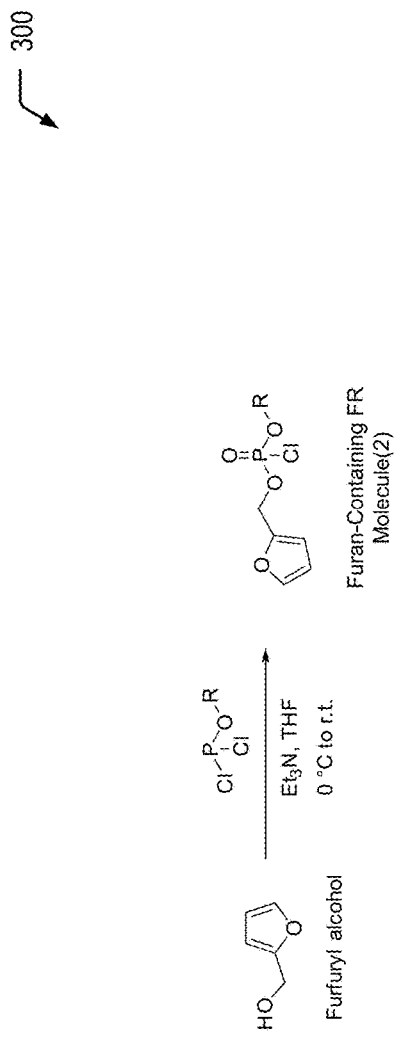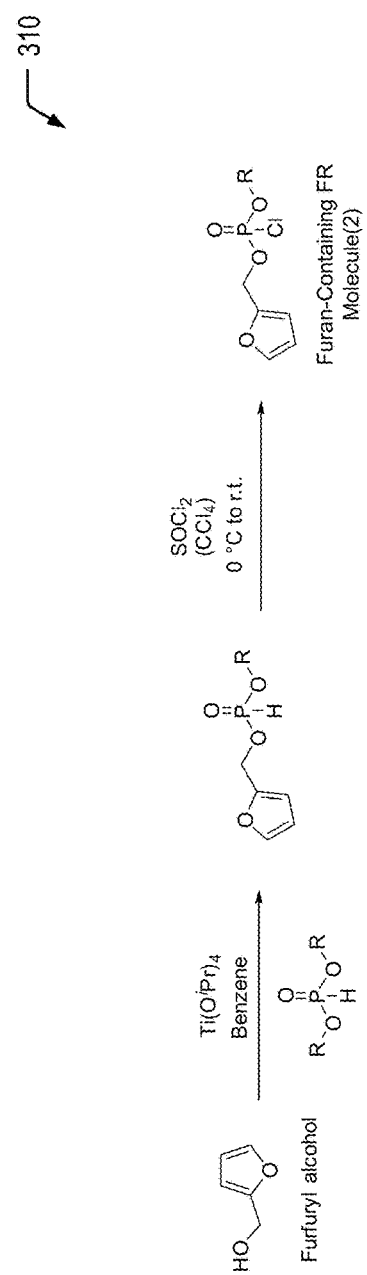

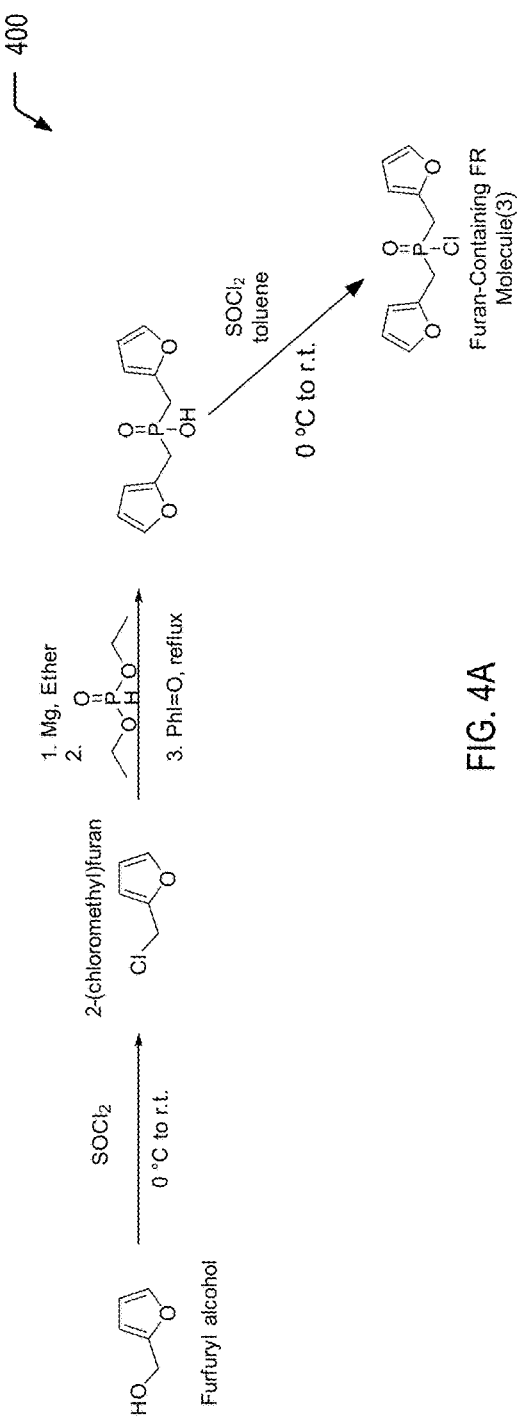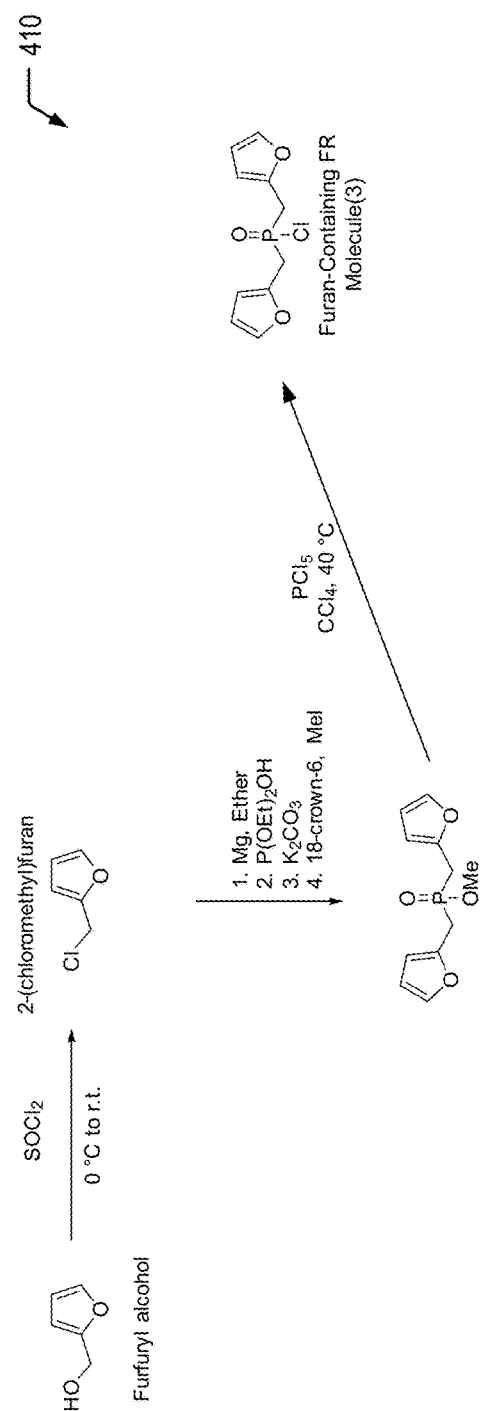
FIG. 4A
FIG. 4B

FURAN-CONTAINING FLAME RETARDANT MOLECULES

BACKGROUND

Plastics are typically derived from a finite and dwindling supply of petrochemicals, resulting in price fluctuations and supply chain instability. Replacing non-renewable petroleum-based polymers with polymers derived from renewable resources may be desirable. However, there may be limited alternatives to petroleum-based polymers in certain contexts. To illustrate, particular plastics performance standards may be specified by a standards body or by a regulatory agency. In some cases, alternatives to petroleum-based polymers may be limited as a result of challenges associated with satisfying particular plastics performance standards.

SUMMARY

In a particular embodiment, a furan-containing flame retardant molecule is disclosed. The furan-containing flame retardant molecule includes a furan moiety bonded to a phosphorus moiety via a phosphoryl linkage or via a phosphinyl linkage.

In another embodiment, a process of forming a furan-containing flame retardant molecule is disclosed. The furan-containing flame retardant molecule includes a furan moiety bonded to a phosphorus moiety via a phosphoryl linkage or via a phosphinyl linkage.

In yet another embodiment, a process of forming a furan-containing flame retardant molecule from furfuryl alcohol is disclosed. The furan-containing flame retardant molecule includes a methylfuran group bonded to a phosphorus moiety via a phosphoryl linkage or via a phosphinyl linkage.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

FIG. 1 is a diagram showing examples of furan-containing flame retardant molecules, according to one embodiment.

FIGS. 3A and 3B are chemical reaction diagrams showing alternative embodiments of processes of forming the second furan-containing flame retardant molecule depicted in FIG. 1.

FIGS. 4A and 4B are chemical reaction diagrams showing alternative embodiments of processes of forming the third furan-containing flame retardant molecule depicted in FIG. 1.

DETAILED DESCRIPTION

Figure 2:
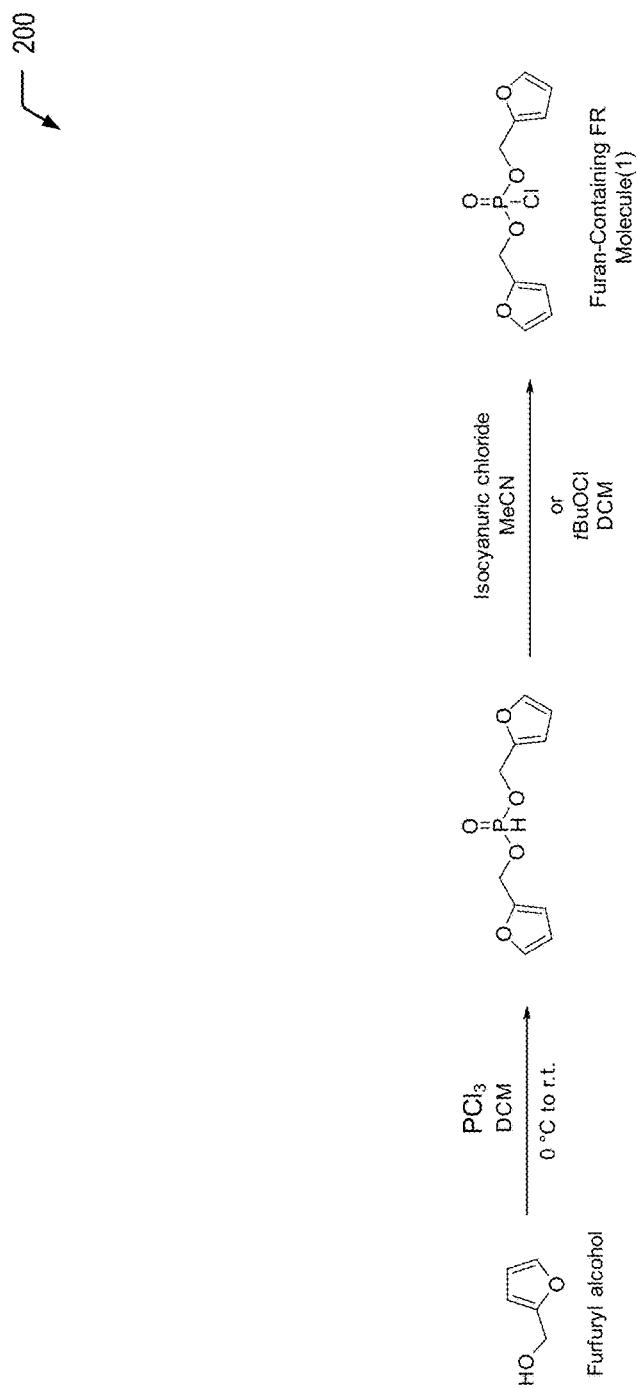
FIG. 2 is a chemical reaction diagram showing a process of forming the first furan-containing flame retardant molecule depicted in FIG. 1, according to one embodiment.

The present disclosure describes furan-containing flame retardant (FR) molecules and methods of forming furan-containing FR molecules. The present disclosure also describes applications of the furan-containing FR molecules. The furan-containing FR molecules of the present disclosure include at least one furan moiety bonded to a phosphorus moiety via a phosphoryl linkage or via a phosphinyl linkage. Bonding the phosphorus moiety to the furan moiety (or moieties) imparts flame retardant characteristics to the molecules. Further, when the furan-containing FR molecules are incorporated into a polymeric material or bonded to a particle, each furan moiety represents a diene group that may be used for subsequent cross-linking (e.g., via a Diels-Alder reaction with a dienophile-functionalized material).

The furan-containing FR molecules of the present disclosure may be synthesized from furfuryl alcohol. Furfuryl alcohol represents a renewable feedstock material that may be synthesized from biomass (e.g., via catalytic reduction of furfural derived from corn stover and/or sugar cane bagasse). Accordingly, the furan-containing FR molecules of the present disclosure may be used to increase the renewable content in a polymeric material, while simultaneously imparting flame retardant characteristics and potentially reducing or eliminating the need for flame retardant additives.

The furfuryl alcohol-derived furan-containing FR molecules of the present disclosure are synthesized to incorporate a phosphorus group in order to impart flame retardant properties. The furfuryl alcohol-derived furan-containing FR molecules of the present disclosure may have one or two furan moieties in order to allow for variable control over the potential extent of subsequent cross-linking. When the furan moiety is a methylfuran group, each furan moiety can either be linked to the phosphorus moiety directly through the methylene carbon via a phosphinate linkage (a C—P linkage, also referred to as a phosphinyl linkage) or through the oxygen of furfuryl alcohol via a phosphate linkage (a C—O—P linkage, also referred to as a phosphoryl linkage).

In some cases, the furan-containing FR molecules of the present disclosure may be utilized to form a cross-linkable flame retardant (CLFR) polymeric/oligomeric material. In other cases, the furan-containing FR molecules of the present disclosure may be utilized to form a cross-linkable flame retardant particle (CLFRP). In both cases, the furan moieties represent available cross-linking locations (e.g., for reversibly cross-linking to a renewable/non-renewable polymeric material or to a dienophile-functionalized particle). Further, in the case of CLFRPs, rather than adding separate silica particles and flame retardant particles/molecules, the flame retardant moiety is bonded to the particle itself.

Referring to FIG. 1, a diagram 100 illustrates examples of furan-containing FR molecules according to the present disclosure. FIG. 1 illustrates four examples of furan-containing FR molecules that include one or more furan moieties bonded to a phosphorus moiety via one or more phosphoryl linkages or via one or more phosphinyl linkages. As described further herein, the furan-containing FR molecules illustrated in FIG. 1 may be formed from renewable furfuryl alcohol.

In FIG. 1, a first furan-containing FR molecule (identified as "Furan-Containing FR Molecule(1)" in FIG. 1) includes two furan moieties (e.g., two methylfuran groups) and a chloride group. A second furan-containing FR molecule (identified as "Furan-Containing FR Molecule(2)" in FIG. 1) includes one furan moiety (e.g., one methylfuran group) and a chloride group. The first furan-containing FR molecule of FIG. 1 and the second furan-containing FR molecule depicted in FIG. 1 represent examples of molecules having one or more furan moieties bonded to a phosphorus moiety via phosphoryl linkages (i.e., via the oxygen from the furfuryl alcohol precursor). The first furan-containing FR molecule of FIG. 1 represents a difuran-functionalized phosphate molecule, having two furan moieties (e.g., methylfuran groups) bonded to the phosphorus moiety via phosphoryl linkages. The second furan-containing FR molecule of FIG. 1 represents a monofuran-functionalized phosphate molecule, having a single furan moiety (e.g., a single methylfuran group) bonded to the phosphorus moiety via a phosphoryl linkage. The number of furan moieties represents the number of potential cross-linking locations. As described further herein, a single furan moiety provides a single potential cross-linking location, and two furan moieties provide two potential cross-linking locations (e.g., via a Diels-Alder reaction with a dienophile-functionalized material).

In FIG. 1, a third furan-containing FR molecule (identified as "Furan-Containing FR Molecule(3)" in FIG. 1) includes two furan moieties (e.g., two methylfuran groups) and a chloride group. A fourth furan-containing FR molecule (identified as "Furan-Containing FR Molecule(4)" in FIG. 1) includes a single furan moiety (e.g., a single methylfuran group) and a chloride group. The third furan-containing FR molecule of FIG. 1 and the fourth furan-containing FR molecule depicted in FIG. 1 represent examples of molecules having one or more furan moieties bonded to a phosphorus moiety via phosphinyl linkages. The third furan-containing FR molecule of FIG. 1 represents a difuran-functionalized phosphonate molecule, having two furan moieties (e.g., methylfuran groups) bonded to the phosphorus moiety via phosphinyl linkages. The fourth furan-containing FR molecule of FIG. 1 represents a monofuran-functionalized phosphonate molecule, having a single furan moiety (e.g., a single methylfuran group) bonded to the phosphorus moiety via a phosphinyl linkage.

The first furan-containing FR molecule of FIG. 1 may be formed according to the process described further herein with respect to FIG. 2. In some cases, as described further herein with respect to FIG. 6, the two furan moieties may be used to form two terminal furan moieties at each end of a cross-linkable flame retardant (CLFR) oligomer/polymer. Each terminal furan moiety represents a diene group that may (reversibly) react with a dienophile group of another material via a Diels-Alder reaction. In other cases, as described further herein with respect to FIG. 10, the first furan-containing FR molecule of FIG. 1 may be used to form a CLFR particle (CLFRP) having two furan moieties bonded to a surface of a hydroxyl-containing particle (e.g., a silica particle) via a chemical reaction of the chloride group and the hydroxyl group. As shown in the example of FIG. 11, the two furan moieties of the CLFRP represent two potential locations for cross-linking reactions with dienophile groups of a dienophile-functionalized particle.

In some cases, the second furan-containing FR molecule of FIG. 1 may be formed according to the process described further herein with respect to FIG. 3A. In other cases, the second furan-containing FR molecule of FIG. 1 may be formed according to the process described further herein with respect to FIG. 3B. As described further herein with respect to FIG. 7, the single furan moiety may be used to form a single terminal furan moiety at each end of a CLFR oligomer/polymer. The terminal furan moiety represents a diene group that may (reversibly) react with a dienophile group of another material via a Diels-Alder reaction. In other cases, the second furan-containing FR molecule of FIG. 1 may be used to form a CLFRP having one furan moiety bonded to a surface of a hydroxyl-containing particle (e.g., a silica particle) via a chemical reaction of the chloride group and the hydroxyl group. The single furan moiety of the CLFRP represents one potential location for a reversible cross-linking reaction with a dienophile group of a dienophile-functionalized material (e.g., a dienophile-functionalized particle in the example of FIG. 11).

In some cases, the third furan-containing FR molecule of FIG. 1 may be formed according to the process described further herein with respect to FIG. 4A. In other cases, the third furan-containing FR molecule of FIG. 1 may be formed according to the process described further herein with respect to FIG. 4B. In some cases, as described further herein with respect to FIG. 8, the two furan moieties may be used to form two terminal furan moieties at each end of a CLFR oligomer/polymer. Each terminal furan moiety represents a diene group that may (reversibly) react with a dienophile group of another material via a Diels-Alder reaction. In other cases, the third furan-containing FR molecule of FIG. 1 may be used to form a CLFRP, having two furan moieties, bonded to a surface of a hydroxyl-containing particle (e.g., a silica particle) via a chemical reaction of the chloride group and the hydroxyl group. The two furan moieties of the CLFRP represent two potential locations for reversible cross-linking reactions with dienophile groups of a dienophile-functionalized material (e.g., a dienophile-functionalized particle in the example of FIG. 11).

Figure 5A:
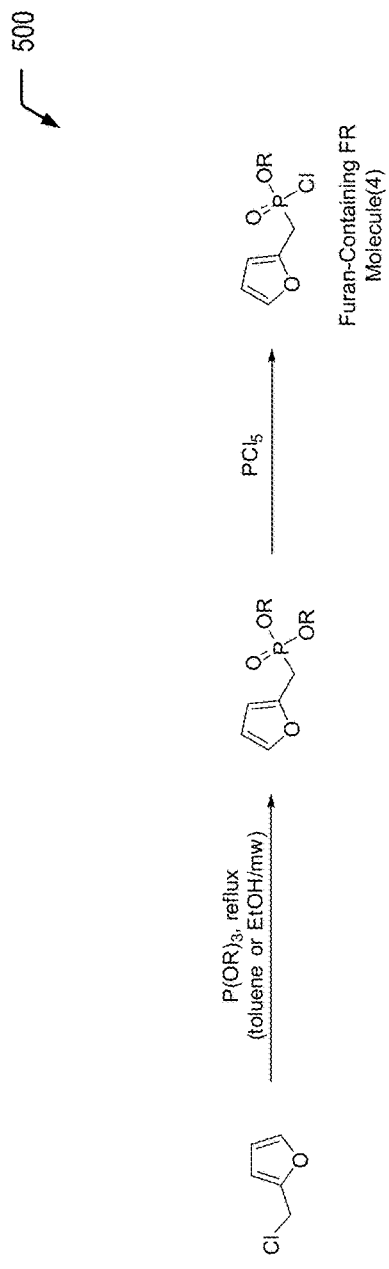
FIGS. 5A and 5B are chemical reaction diagrams showing alternative embodiments of processes of forming the fourth furan-containing flame retardant molecule depicted in FIG. 1.

In some cases, the fourth furan-containing FR molecule of FIG. 1 may be formed according to the process described further herein with respect to FIG. 5A. In other cases, the fourth furan-containing FR molecule of FIG. 1 may be formed according to the process described further herein with respect to FIG. 5B. As described further herein with respect to FIG. 9, the single furan moiety may be used to form a single terminal furan moiety at each end of a CLFR oligomer/polymer. The terminal furan moiety represents a diene group that may (reversibly) react with a dienophile group of another material via a Diels-Alder reaction. In other cases, the fourth furan-containing FR molecule of FIG. 1 may be used to form a CLFRP, having one furan moiety, bonded to a surface of a hydroxyl-containing particle (e.g., a silica particle) via a chemical reaction of the chloride group and the hydroxyl group. The single furan moiety of the CLFRP represents one potential location for a reversible cross-linking reaction with a dienophile group of a dienophile-functionalized material (e.g., a dienophile-functionalized particle in the example of FIG. 11).

Thus, FIG. 1 illustrates examples of furan-containing FR molecules that include one or more furan moieties bonded to a phosphorus moiety via one or more phosphoryl linkages or via one or more phosphinyl linkages. FIG. 1 illustrates that the furan-containing FR molecule can either possess one or two furan moieties in order to allow for variable control over the potential extent of subsequent cross-linking, as described further herein.

Referring to FIG. 2, a chemical reaction diagram 200 illustrates an example of a process of forming the first furan-containing flame retardant molecule depicted in FIG. 1, according to one embodiment. FIG. 2 illustrates that the first furan-containing FR molecule depicted in FIG. 1 may be synthesized from the renewable furan moiety, furfuryl alcohol.

FIG. 2 illustrates an example of a process of forming a difuran-functionalized phosphate molecule from furfuryl alcohol. In the first chemical reaction depicted in FIG. 2, furfuryl alcohol is chemically reacted with phosphorus trichloride ($PCl_3$) to form a phosphine oxide intermediate material. As an example, the first chemical reaction may include dissolving phosphorus oxychloride in a suitable solvent, such as dichloromethane (DCM), with the reaction proceeding from 0° C. to room temperature. As a prophetic example, phosphorus trichloride and DCM may be placed in a flask immersed in an ice bath and equipped with a magnetic stirrer and a condenser (the head of which is connected to a water vacuum pump). Furfuryl alcohol, diluted with DCM may be added dropwise to the mixture. The mixture may be stirred for another 10 minutes, and DCM may be subsequently evaporated.

As a prophetic example, $PCl_3$ (1.0 eq.) and freshly dried toluene may be added to a two-necked round-bottom flask flushed with inert gas. The reaction mixture may be stirred at 0° C. Furfuryl alcohol (2.0 eq.), dimethylphenylamine (2.16 eq.), and toluene may be added to a separate two-necked round-bottom flask flushed with inert gas. The furfuryl alcohol mixture may be added dropwise to the $PCl_3$ solution over 1 hour. The resulting mixture may be stirred at ambient temperature for 1 additional hour. Upon completion, water may be added carefully and the mixture may be stirred for 30 min at ambient temperature. The crude product may be extracted with $Et_2O$ (2×) and washed with water (2×). The organic phase may be dried ($MgSO_4$) and the solvent may be removed in vacuo, and may be dried or purified further.

In the second chemical reaction depicted in FIG. 2, the phosphine oxide intermediate material is chemically reacted with either isocyanuric chloride or tert-butyl hypochlorite (tBuOCl) to form bis(furylmethylene)phosphoryl chloride, corresponding to the first furan-containing FR molecule of FIG. 1. In the case of isocyanuric chloride, the second chemical reaction may include a suitable solvent such as acetonitrile (MeCN). In the case of tert-butyl hypochlorite, the second chemical reaction may include a suitable solvent such as DCM. FIG. 2 illustrates that the resulting molecule has a functional phosphorus group with two furan groups available for subsequent reversible cross-linking.

As a prophetic example (using isocyanuric chloride), bis(furan-2-ylmethyl) phosphite (1.0 eq.) in either dry acetonitrile (MeCN), toluene, or dichloromethane (DCM) may be added to a solution of trichloroisocyanuric acid (0.33 eq.), N-chlorosuccinimide (1.0 eq.), or tert-butyl hypochlorite (1.0 eq.) in the same solvent at room temperature, under an $N_2$ atmosphere. Upon the formation of a precipitate, the reaction may be stirred at room temperature for an additional 2 hours. Upon completion of the reaction, as determined by $^{31}P$ NMR, the reaction mixture was passed through a 0.45 μm Whatman syringe filter and concentrated under vacuum. A similar procedure may be utilized in the case of tert-butyl hypochlorite.

Thus, FIG. 2 illustrates an example of a process of forming a furan-containing FR molecule from renewable furfuryl alcohol. In the example of FIG. 2, furfuryl alcohol is used to form a furan-containing FR molecule having two furan moieties bonded to a phosphorus moiety via two phosphoryl linkages. As described further herein, the phosphorus moiety includes a chloride group for bonding (e.g., via chemical reaction with a hydroxyl group), and the two furan moieties provide two potential locations for Diels-Alder reactions with dienophile group(s) of another material.

FIGS. 3A and 3B are chemical reaction diagrams showing alternative embodiments of processes of forming the second furan-containing flame retardant molecule depicted in FIG. 1. Referring to FIG. 3A, a first chemical reaction diagram 300 illustrates a first embodiment of a process of forming the second furan-containing flame retardant molecule depicted in FIG. 1. Referring to FIG. 3B, a second chemical reaction diagram 310 illustrates an alternative embodiment of a process of forming the second furan-containing flame retardant molecule depicted in FIG. 1.

FIG. 3A illustrates a first example of a process of forming a monofuran-functionalized phosphonate molecule. FIG. 3A illustrates a one-step process via reaction of furfuryl alcohol with dichlorophosphate via careful addition and stoichiometric control. The alkyl (R) groups may include ethyl groups, methyl groups, propyl groups, isopropyl groups, or phenyl groups, among other alternatives. The one-step process may utilize triethylamine ($Et_3N$) and a suitable solvent, such as tetrahydrofuran (THF), and the chemical reaction may be performed from 0° C. to room temperature. FIG. 3A illustrates that the resulting molecule is functionalized with one furan moiety for cross-linking and one chloride for further bonding.

As a prophetic example, to a stirred solution that may include furfuryl alcohol (1.0 eq.) and triethylamine (2.0 eq.) in anhydrous THF, phenyl dichlorophosphate (1.3 eq.) may be added dropwise at 0° C., and the reaction mixture may be stirred at ambient temperature for 2 hours or it may be heated up to reflux (60-65° C.) for an extended reaction time (4 hours). The reaction mixture may be cooled to ambient temperature and filtered to remove the triethylamine hydrochloride salt. The solvents of the filtrate may be removed in vacuo and the product may be purified by fractional distillation.

FIG. 3B illustrates a second example of a process of forming the monofuran-functionalized phosphate molecule. FIG. 3B illustrates an alternative in which furfuryl alcohol can be reacted with titanium (IV) isopropoxide and phophonic acid dialkylester or diphenylester as a pseudotransesterification. The R groups may include ethyl groups, methyl groups, propyl groups, isopropyl groups, or phenyl groups, among other alternatives. The resulting molecule may be reacted with thionyl chloride to give a furan-containing FR molecule with one furan moiety for cross-linking and one chloride for further bonding. In the first chemical reaction, titanium (IV) isopropoxide may be dissolved in a suitable solvent, such as benzene. In the second chemical reaction, thionyl chloride may be dissolved in a suitable solvent, such as carbon tetrachloride ($CCl_4$), and the chemical reaction may be performed from 0° C. to room temperature.

As a prophetic example, Dialkyl or diaryl phosphite 1 (5.5 mmol) may be added to the solution of the titanium (IV) isopropoxide (11 mmol) in furfuryl alcohol (excess). This solution may be diluted with benzene. The reaction mixture may be heated 40° C. until completion. The mixture may be poured into water, extracted with $CH_2Cl_2$ (3×), dried over $MgSO_4$, and solvent and volatile components may be removed in vacuo. The products may be purified by fractional distillation or recrystallization. The product from the first step (1.0 eq.), in dry acetonitrile (MeCN), toluene, or dichloromethane (DCM), may be added to a solution of trichloroisocyanuric acid (0.33 eq.), N-chlorosuccinimide (1.0 eq.), or tert-butyl hypochlorite (1.0 eq.) in the same solvent at room temperature, under an $N_2$ atmosphere. Upon the formation of a precipitate, the reaction may be stirred at room temperature for an additional 2 hours. Upon completion of the reaction, as determined by $^{31}P$ NMR, the reaction mixture may be passed through a 0.45 μm Whatman syringe filter and concentrated under vacuum.

FIGS. 3A and 3B illustrate examples of alternative processes of forming a furan-containing flame retardant molecule from renewable furfuryl alcohol. In the examples of FIGS. 3A and 3B, furfuryl alcohol is used to form a furan-containing FR molecule having a single furan moiety bonded to a phosphorus moiety via a phosphoryl linkage. As described further herein, the phosphorus moiety includes a chloride group for bonding (e.g., via chemical reaction with a hydroxyl group), and the single furan moiety provides one potential location for a Diels-Alder reaction with a dienophile group of another material.

FIGS. 4A and 4B are chemical reaction diagrams showing alternative embodiments of processes of forming the third furan-containing FR molecule depicted in FIG. 1. Referring to FIG. 4A, a first chemical reaction diagram 400 illustrates a first embodiment of a process of forming the third furan-containing FR molecule depicted in FIG. 1. Referring to FIG. 4B, a second chemical reaction diagram 410 illustrates an alternative embodiment of a process of forming the third furan-containing FR molecule depicted in FIG. 1.

FIG. 4A illustrates a first example of a process of forming a bisfuran-functionalized phosphine oxide molecule. In the first chemical reaction depicted in FIG. 4A, furfuryl alcohol is chemically reacted with thionyl chloride to form 2-(chloromethyl)furan, and the chemical reaction may be performed from 0° C. to room temperature. Alternatively, bromomethylfuran can be synthesized from commercially available reagents and can be used similarly to chloromethylfuran. In the second chemical reaction depicted in FIG. 4A, a Grignard reagent is prepared and reacted with the appropriate phosphonic acid diester to form a phosphinic acid intermediate material. In the third chemical reaction of FIG. 4A, the phosphinic acid intermediate material is reacted with thionyl chloride, resulting in the third furan-containing FR molecule of FIG. 1.

As a prophetic example, furfuryl alcohol may be added, dropwise, to an excess of thionyl chloride at 0° C. The reaction mixture may be warmed to ambient temperature or reflux and stirred until completion as indicated by TLC. The excess thionyl chloride may be removed in vacuo and the crude product may be used in the next step without further purification. To a stirred suspension of activated magnesium turnings in diethyl ether may be added 2-chloromethylfuran, dropwise, at 0° C. Upon completion of the addition, the reaction mixture may be heated to reflux for 1 hour. The reaction mixture is then cooled to room temperature and may be added via cannula to a stirred solution of phosphonic acid diethyl ester at 0° C. The reaction mixture may be warmed to room temperature and stirred until completion, poured into water, and extracted with diethyl ether. The combined organic fractions may be dried over $MgSO_4$, filtered, and the solvents removed in vacuo. The product may be purified by distillation or recrystallization. The phosphine oxide product may be added to a suspension of PhIO in an organic solvent that may include THF or toluene. The reaction mixture may be stirred for 20 minutes to 12 hours at reflux. The reaction mixture may then be diluted with ether and extracted of 5% $NaHCO_3$ water solution. The organic layer may be dried over $MgSO_4$, evaporated and separated by chromatography. The water layer may be acidified with conc. HCl and extracted with ether. The combined ether solutions may be dried over $MgSO_4$, filtered and evaporated to yield the product. The bis(methyl)furan phosphine oxide may be added, dropwise, to an excess of thionyl chloride (or oxalyl chloride, or isocyanuric chloride) at 0° C. The reaction mixture may be warmed to ambient temperature or reflux and stirred until completion as indicated by TLC. The excess thionyl chloride may be removed in vacuo and the crude product may be purified by fractional distillation.

FIG. 4B illustrates a second example of a process of forming the bisfuran-functionalized phosphine oxide molecule. In the first chemical reaction depicted in FIG. 4A, furfuryl alcohol is chemically reacted with thionyl chloride to form 2-(chloromethyl)furan, and the chemical reaction may be performed from 0° C. to room temperature. Alternatively, bromomethylfuran can be synthesized from commercially available reagents and can be used similarly to chloromethylfuran. In the second chemical reaction depicted in FIG. 4B, the 2-(chloromethyl)furan product formed from the furfuryl alcohol may be used to form a phosphinic ester intermediate material. The third chemical reaction of FIG. 4B illustrates that the phosphinic ester intermediate material is reacted with phosphorus pentachloride ($PCl_5$), resulting in the third furan-containing FR molecule of FIG. 1.

As a prophetic example, to a stirred suspension of activated magnesium turnings in diethyl ether may be added 2-chloromethylfuran (synthesized as described previously), dropwise, at 0° C. Upon completion of the addition, the reaction mixture may be heated to reflux for 1 hour. The reaction mixture is then cooled to room temperature and may be added via cannula to a stirred solution of phosphonic acid diethyl ester at 0° C. The reaction mixture may be warmed to room temperature and stirred until completion, poured into water, and extracted with diethyl ether. The combined organic fractions may be dried over $MgSO_4$, filtered, and the solvents removed in vacuo. The product may be purified by distillation or recrystallization. The phosphinic acid product may be stirred with a suspension of potassium carbonate in an organic solvent such as DMF or THF and heated to a temperature that may be between 60-100° C. Methyl iodide and 18-crown-6 may be added dropwise to the reaction mixture, and may be stirred until completion. The reaction mixture may be poured into water, and extracted with diethyl ether. The combined organic fractions may be dried over MgSO$_4$, filtered, and the solvents removed in vacuo. The product may be purified by distillation or recrystallization. To a solution of the product from the previous step in CCl$_4$ may be added PCl$_5$ (excess) at 0° C. under an inert atmosphere. The mixture may be allowed to warm up to room temperature and may be stirred for an additional day. The solvent is removed in vacuo and the residue may be distilled to give the product.

Thus, FIGS. 4A and 4B illustrate alternative processes of forming a furan-containing flame retardant molecule from renewable furfuryl alcohol. In the examples of FIGS. 4A and 4B, furfuryl alcohol is used to form a furan-containing FR molecule having two furan moieties bonded to a phosphorus moiety via two phosphinyl linkages. As described further herein, the phosphorus moiety includes a chloride group for bonding (e.g., via chemical reaction with a hydroxyl group), and the two furan moieties provide two potential locations for Diels-Alder reactions with dieonophile group(s) of another material.

Figure 5B:
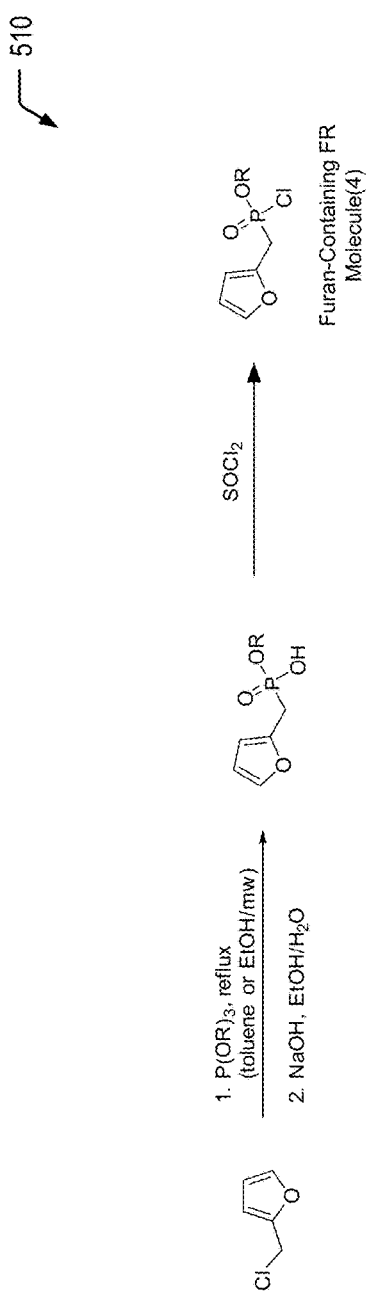

FIGS. 5A and 5B are chemical reaction diagrams showing alternative embodiments of processes of forming the fourth furan-containing FR molecule depicted in FIG. 1. Referring to FIG. 5A, a first chemical reaction diagram 500 illustrates a first embodiment of a process of forming the fourth furan-containing FR molecule depicted in FIG. 1. Referring to FIG. 5B, a second chemical reaction diagram 510 illustrates an alternative embodiment of a process of forming the fourth furan-containing FR molecule depicted in FIG. 1.

FIG. 5A illustrates a first example of a process of forming the single phosphonate-linked furan phosphoryl chloride, methylenefuran-phosphonyl chloride. In the first chemical reaction depicted in FIG. 5A, 2-(chloromethyl)furan (which may be synthesized as described herein with respect to FIGS. 4A and 4B) is chemically reacted with a trialkylphosphite or a triphenylphosphite to form a phosphonyl ester. R groups may include ethyl groups, methyl groups, propyl groups, isopropyl groups, or phenyl groups, among other alternatives. In the second chemical reaction depicted in FIG. 5B, the phosphonyl ester is reacted with phosphorus pentachloride to form the fourth furan-containing FR molecule depicted in FIG. 1.

As a prophetic example, 2-(chloromethyl)furan (1 eq.) and trialkyl phosphite may be added to a reaction vessel, which may include an organic solvent such as toluene, THF, ethanol, or DMF, and may also contain a compound such as alumina. The reaction may be heated to reflux or up to 180° C. if done using neat conditions. The reaction mixture may also be irradiated by microwaves for a short period to increase the reaction rate. The reaction may be cooled to room temperature and the excess trialky phosphite may be removed in vacuo or it may be washed with DCM, and dried for CaCl$_2$ prior to filtration and having the solvents removed in vacuo. The phosphonate may be purified by fractional distillation. To a solution of the phosphonate product may be added PCl$_5$ (excess) at 0° C. under an inert atmosphere. The reaction may be performed in a solvent such as CCl$_4$. The mixture may be allowed to warm up to room temperature and may be stirred for an additional day. The solvent is removed in vacuo and the residue may be distilled to give the product.

FIG. 5B illustrates a second example of a process of forming the single phosphonate-linked furan phosphoryl chloride, methylenefuran-phosphonyl chloride. In the first chemical reaction depicted in FIG. 5B, 2-(chloromethyl) furan (synthesized as described herein with respect to FIGS. 4A and 4B) is reacted with a trialkylphosphite or a triphenylphosphite and quenching under aqueous basic conditions to form an alternative intermediate material. R groups may include ethyl groups, methyl groups, propyl groups, isopropyl groups, or phenyl groups, among other alternatives. The second chemical reaction of FIG. 5B illustrates that the intermediate material is then reacted with thionyl chloride to form the fourth furan-containing FR molecule depicted in FIG. 1.

As a prophetic example, a methylfuryl phosphonate may be generated in a manner similar to that of the phosphonate intermediate used to synthesize the fourth furan-containing FR molecule. Dialkyl benzylphosphonate (1.0 eq.) may be quickly added to a solution of bromodimethyl borane (1.0 eq.) in an organic solvent that may be toluene. The reaction mixture may be warmed to room temperature and stirred overnight. The solvent and volatile byproducts may be removed in vacuo and give a slightly yellow viscous oil. To a solution of the phosphonic acid product may be added SOCl$_2$ (excess) at 0° C. The mixture may be allowed to warm up to room temperature, or heated to 40° C. and may be stirred for an additional day. The solvent is removed in vacuo and the residue may be distilled to give the product.

Thus, FIGS. 5A and 5B illustrate alternative processes of forming a furan-containing FR molecule from renewable furfuryl alcohol. In the examples of FIGS. 5A and 5B, furfuryl alcohol is used to form a furan-containing FR molecule having a single furan moiety bonded to a phosphorus moiety via a phosphinyl linkage. As described further herein, the phosphorus moiety includes a chloride group for bonding (e.g., via chemical reaction with a hydroxyl group), and the single furan moiety provides one potential location for a Diels-Alder reaction with a dienophile group of another material.

FIGS. 6-10 illustrate example applications of the furan-containing FR molecules depicted in FIG. 1. In some cases, as illustrated and described further herein with respect to FIGS. 6-9, the furan-containing FR molecules of the present disclosure may be utilized to form a CLFR polymer with terminal furan groups. The terminal furan groups act as dienes and will react with a polymeric material that is functionalized with dienophile groups. An illustrative, non-limiting example of a dienophile includes a succinimide or succinic anhydride-functionalized polymer, and the resulting cross-linking reaction can be rendered reversible under specific thermal conditions.

Figure 10:
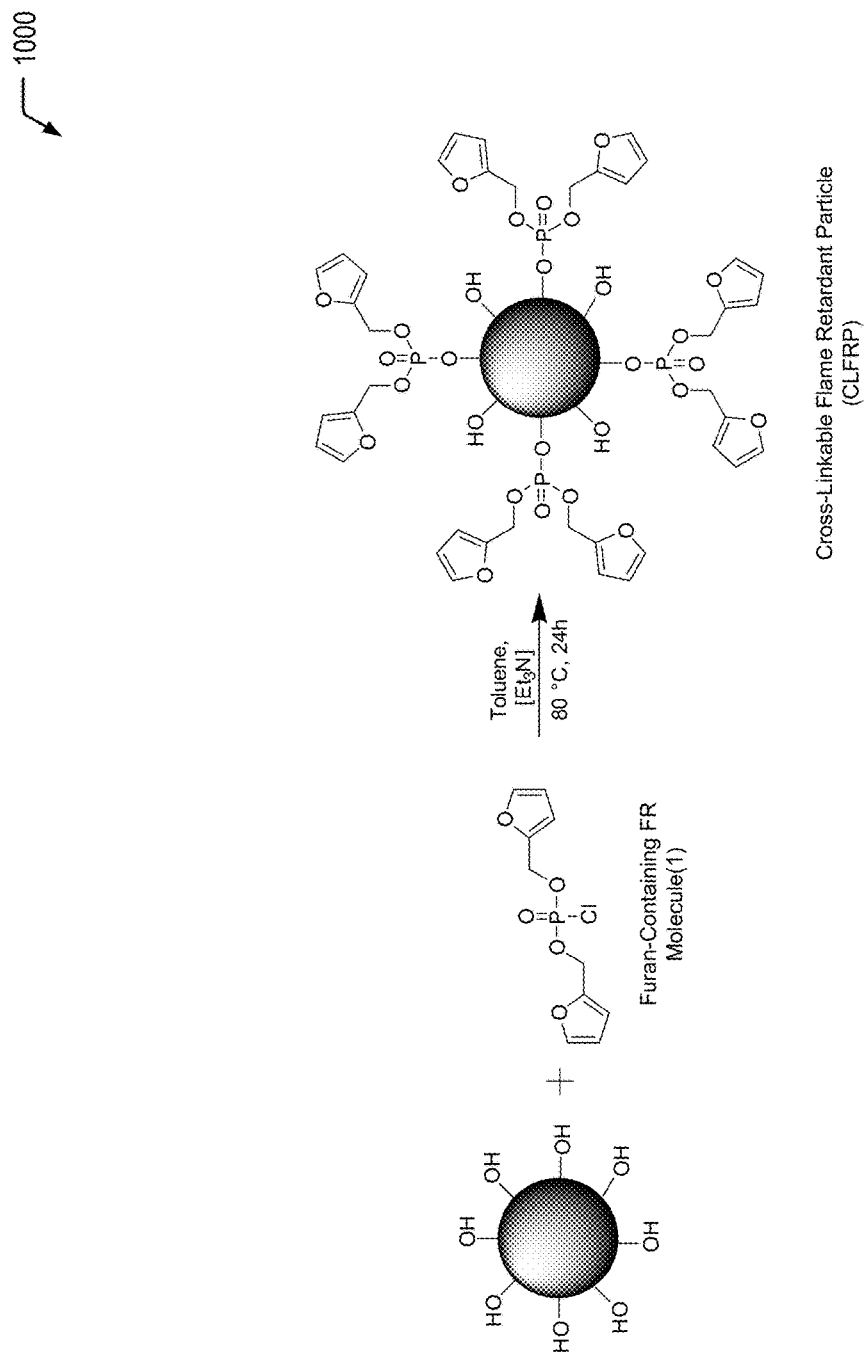
FIG. 10 is a chemical reaction diagram showing a particular embodiment of a process of utilizing the first furan-containing flame retardant molecule of FIG. 1 to form a cross-linkable flame retardant particle (CLFRP).
Figure 11:
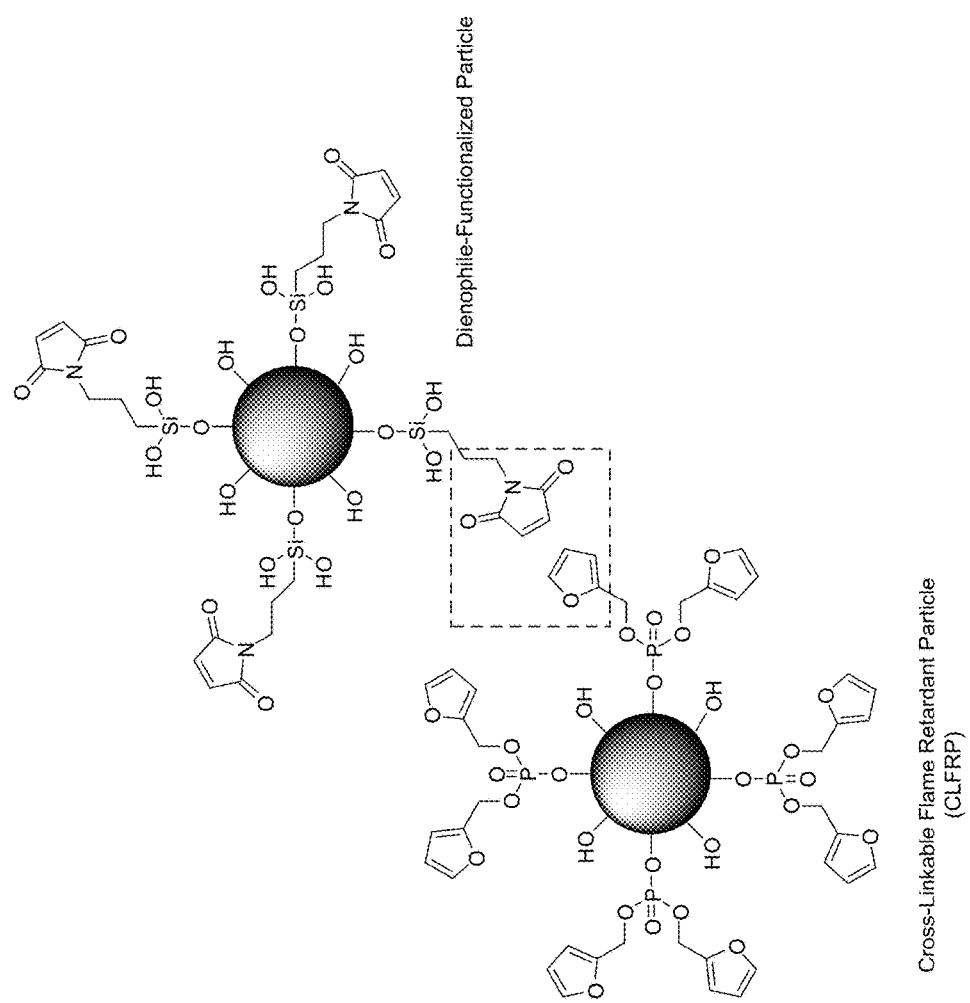
FIG. 11 is a diagram showing an example of a dienophile-functionalized particle that may be reversibly cross-linked to the CLFRP of FIG. 10 via a Diels-Alder reaction.

In other cases, as illustrated and described further herein with respect to FIG. 10, the furan-containing FR molecules of the present disclosure may be utilized to form a cross-linkable flame retardant particle (CLFRP) having diene functionality. In some cases, the CLFRP may be blended with a matrix polymer that contains dienophiles such as a succinic anhydride-functionalized polymer. The resulting cross-linking reaction can be rendered reversible under specific thermal conditions. As another example, FIG. 11 illustrates that the CLFRP of FIG. 10 may be reacted with a corresponding dienophile-modified particle via a Diels-Alder reaction. The reaction may be rendered reversible under specific thermal conditions.

Figure 6:
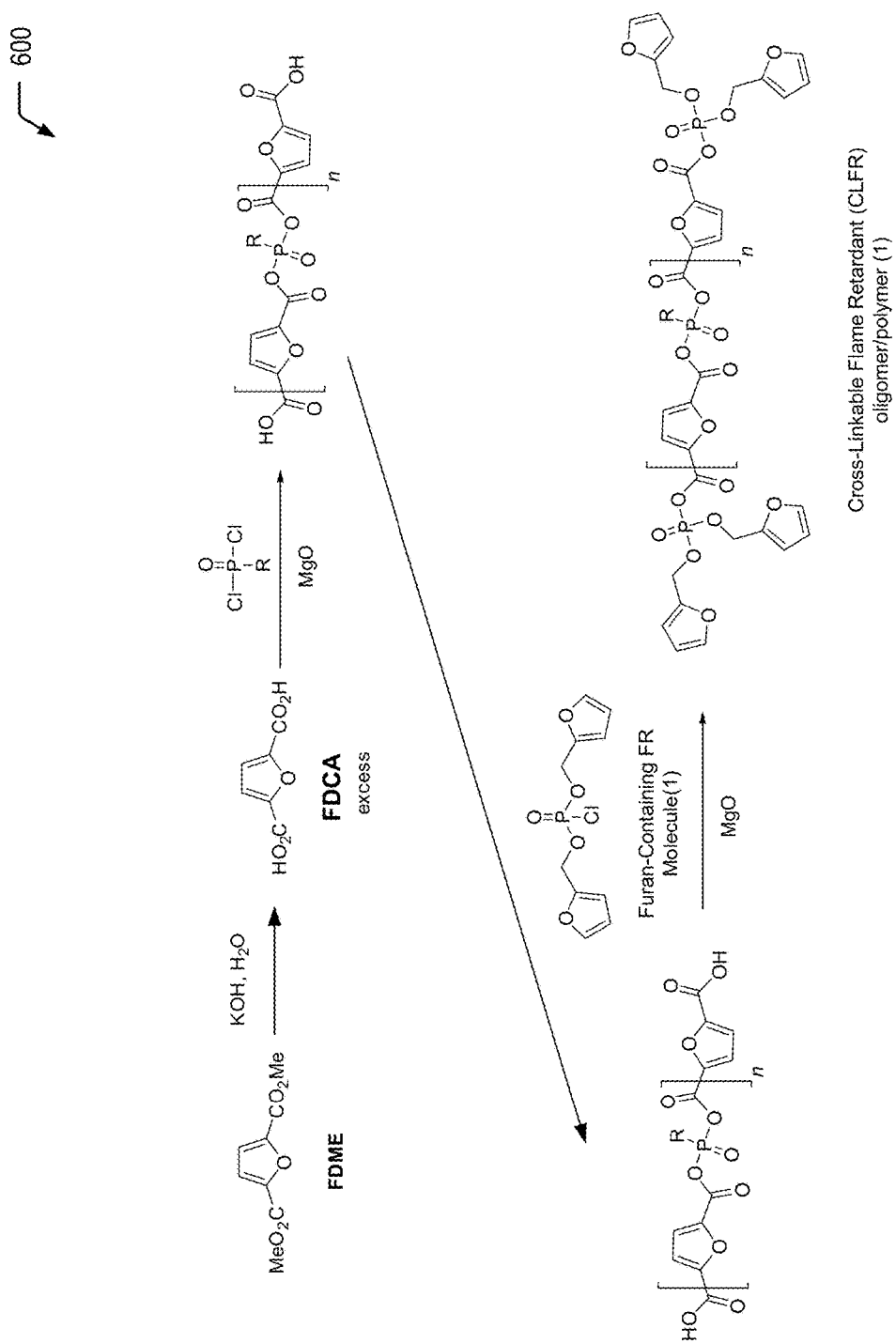
FIG. 6 is a chemical reaction diagram showing a particular embodiment of a process of utilizing the first furan-containing flame retardant molecule depicted in FIG. 1 to form a cross-linkable flame retardant material.

Referring to FIG. 6, a chemical reaction diagram 600 illustrates a particular embodiment of a process of utilizing the first furan-containing FR molecule depicted in FIG. 1 to form a CLFR polymeric/oligomeric material.

The first chemical reactions depicted at the top of FIG. 6 illustrates that furan dicarboxylic methyl ester (FDME) may be used to form a polymeric backbone. In some embodiments, FDME may be produced from renewable resource-derived fructose, thereby increasing the renewable content. The second chemical reaction depicted at the bottom of FIG.

6 illustrates that the first furan-containing FR molecule of FIG. 1 may be used to form a CLFR polymeric/oligomeric material with two terminal furan groups (on each end of the polymer chain). The first furan-containing FR molecule of FIG. 1 may be bound to the terminal ends of the polymeric backbone via a chemical reaction of the chloride group and a hydroxyl group.

As a prophetic example, FDME may be added to an aqueous solution of KOH (3M), and stirred vigorously at 80° C. The reaction may also contain an organic solvent such as THF, and heated to reflux. Upon completion, the reaction mixture may be cooled to room temperature, and extracted with diethyl ether. The combined aqueous layers may be acidified with an aqueous acid such as 3M HCl, and extracted with diethyl ether. The solvents may be removed in vacuo and the crude product may be purified by recrystallization. Subsequently, magnesia (excess) may be added to a mixture of alkyl dichlorophosphate, aryl dichlorophosphate, alkyl dichlorophosphine oxide, or aryl dichlorophosphine oxide (1.0 eq.) and the carboxylic acid (1.01-1.20 eq.). This mixture may be stirred at room temperature for 5-30 minutes. The solid mixture may be washed with dichloromethane (4×25). The solution may be washed subsequently with saturated $NaHCO_3$(aq.), brine, and dried over $MgSO_4$. The solvent may be removed in vacuo, and the crude product purified by any combination of recrystallization, re-precipitation, or chromatography. Magnesia (excess) may be added to a mixture of first furan-containing FR molecule (1.0 eq.) and the carboxylic acid-terminated CLFR material (1.01-1.20 eq.). This mixture may be stirred at room temperature, heated up to 150° C., or be performed in an organic solvent such as THF, dioxane, or DMF for 5-30 minutes. The solid mixture may be washed with dichloromethane (4×25). The solution may be washed subsequently with saturated $NaHCO_3$(aq.), brine, and dried over $MgSO_4$. The solvent may be removed in vacuo, and the crude product purified by any combination of recrystallization, re-precipitation, or chromatography.

The CLFR polymeric material of FIG. 6 may subsequently be used as a Diels-Alder active cross-linker where the two terminal furan groups (on each end of the polymer) act as dienes and may react with polymeric materials functionalized with dienophile functional group(s). For example, a dienophile such as a succinimide-functionalized polymer or a succinic anhydride-functionalized polymer may be used, and the resulting cross-linking reaction can be rendered reversible under specific thermal conditions. The furan groups in the CLFR backbone do not react under standard Diels-Alder reaction conditions as they are deactivated (electron-deficient) due to the flanking carbonyl groups. Thus, only the terminal furan groups react under standard Diels-Alder reaction conditions.

Thus, FIG. 6 illustrates an example of a process of utilizing a furan-containing FR molecule of the present disclosure to form a cross-linkable flame retardant polymeric material. In the example of FIG. 6, the CLFR polymeric material includes two terminal furan groups (on each end of the polymer chain). The terminal furan groups represent diene groups that provide two potential cross-linking locations for reaction with dienophile functional groups of another polymeric material.

Figure 7:
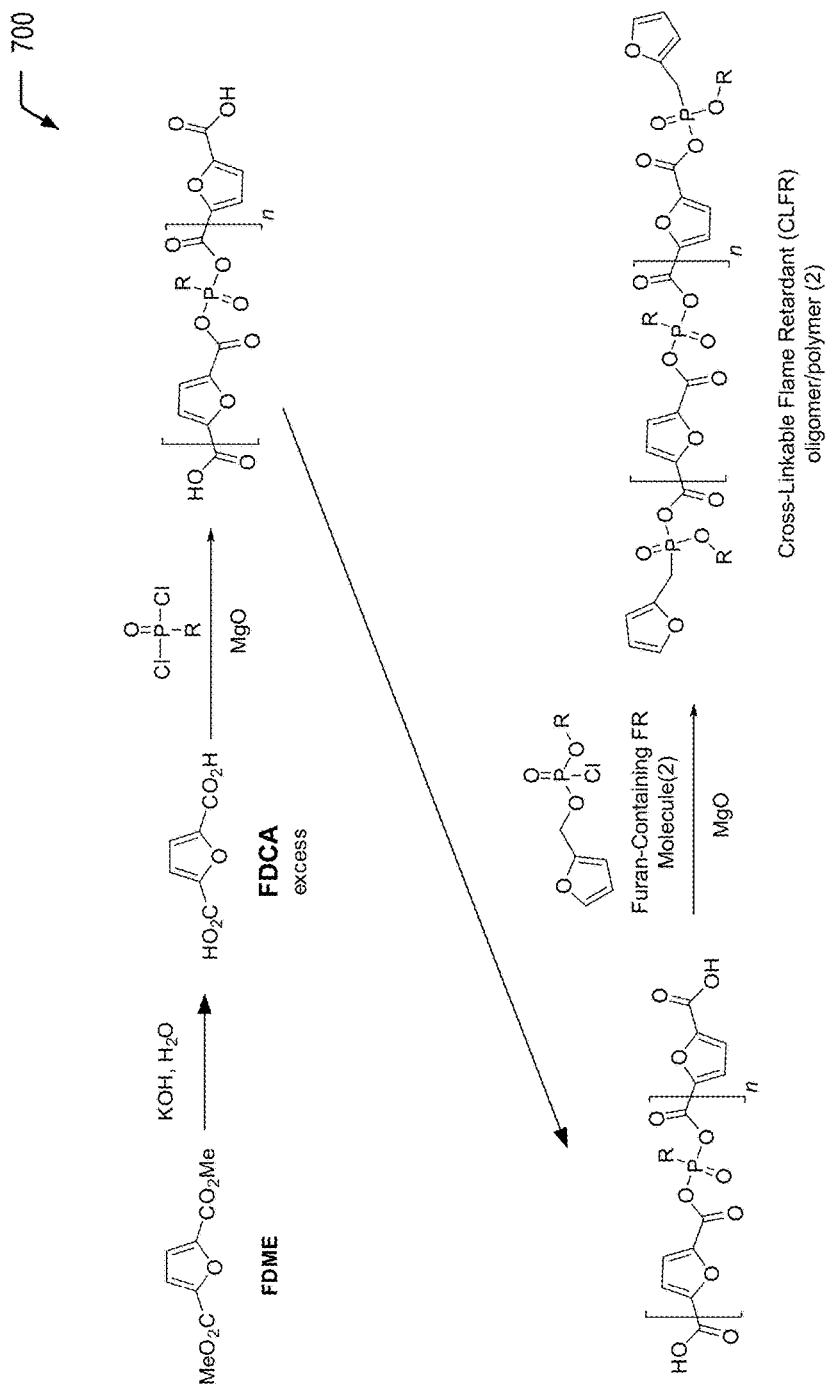
FIG. 7 is a chemical reaction diagram showing a particular embodiment of a process of utilizing the second furan-containing flame retardant molecule depicted in FIG. 1 to form a cross-linkable flame retardant material.

Referring to FIG. 7, a chemical reaction diagram 700 illustrates a particular embodiment of a process of utilizing the second furan-containing FR molecule depicted in FIG. 1 to form a CLFR polymeric/oligomeric material.

The first chemical reactions depicted at the top of FIG. 7 illustrate that FDME may be used to form a polymeric backbone. In some embodiments, FDME may be produced from renewable resource-derived fructose. The second chemical reaction depicted at the bottom of FIG. 7 illustrates that the second furan-containing FR molecule of FIG. 1 may be used to form a CLFR polymeric/oligomeric material with one terminal furan group (on each end of the polymer). The second furan-containing FR molecule of FIG. 1 may be bound to the terminal ends of the polymeric backbone via a chemical reaction of the chloride group and a hydroxyl group.

As a prophetic example, CLFR (2) of FIG. 7 may be prepared in a similar fashion to CLFR (1) of FIG. 6, in which the second furan-containing molecule may be substituted for the first furan-containing molecule during the third and final reaction step (addition of furan-functionalized phosphorous-based end groups of the polymer/oligomer).

The CLFR polymeric material of FIG. 7 may subsequently be used as a Diels-Alder active cross-linker where the terminal furan group (on each end of the polymer) acts as a diene and may react with polymeric materials functionalized with dienophile functional group(s). For example, a dienophile such as a succinimide-functionalized polymer or a succinic anhydride-functionalized polymer may be used, and the resulting cross-linking reaction can be rendered reversible under specific thermal conditions. The furan groups in the CLFR backbone do not react under standard Diels-Alder reaction conditions as they are deactivated (electron-deficient) due to the flanking carbonyl groups. Thus, only the terminal furan group reacts under standard Diels-Alder reaction conditions.

Thus, FIG. 7 illustrates an example of a process of utilizing a furan-containing FR molecule of the present disclosure to form a cross-linkable flame retardant polymeric material. In the example of FIG. 7, the CLFR polymeric material includes one terminal furan group (on each end of the polymer chain). The terminal furan group represents a diene group that provides a potential cross-linking location for reaction with a dienophile functional group of another polymeric material.

Figure 8:
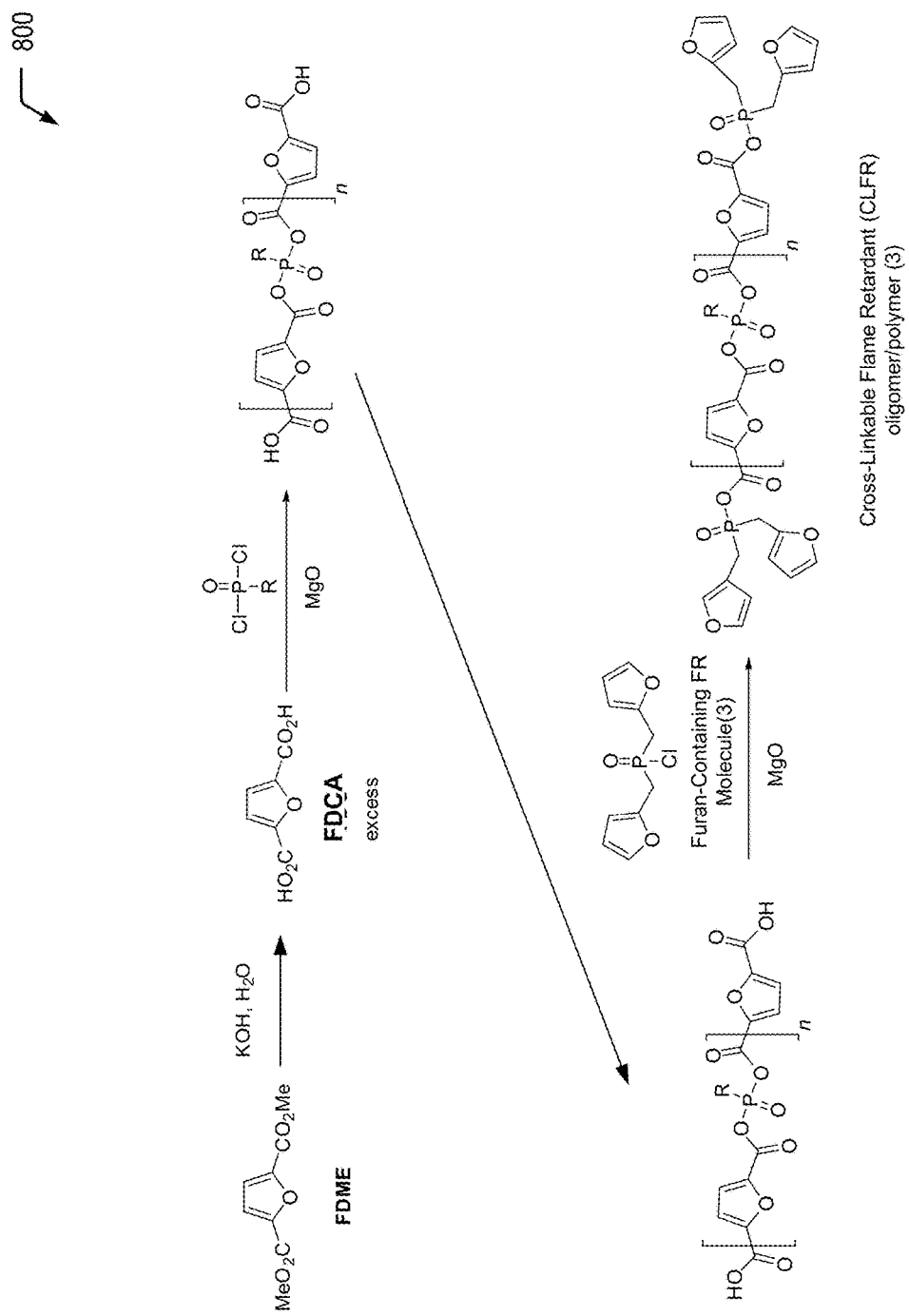
FIG. 8 is a chemical reaction diagram showing a particular embodiment of a process of utilizing the third furan-containing flame retardant molecule depicted in FIG. 1 to form a cross-linkable flame retardant material.

Referring to FIG. 8, a chemical reaction diagram 800 illustrates a particular embodiment of a process of utilizing the third furan-containing FR molecule depicted in FIG. 1 to form a cross-linkable flame retardant material.

The first chemical reactions depicted at the top of FIG. 8 illustrate that FDME may be used to form a polymeric backbone. In some embodiments, FDME may be produced from renewable resource-derived fructose. The second chemical reaction depicted at the bottom of FIG. 7 illustrates that the third furan-containing FR molecule of FIG. 1 may be used to form a CLFR polymeric/oligomeric material with two terminal furan groups (on each end of the polymer chain). The third furan-containing FR molecule of FIG. 1 may be bound to the terminal ends of the polymeric backbone via a chemical reaction of the chloride group and a hydroxyl group.

As a prophetic example, CLFR (3) of FIG. 8 may be prepared in a similar fashion to CLFR (1) of FIG. 6, in which the second furan-containing molecule may be substituted for the first furan-containing molecule during the third and final reaction step (addition of furan-functionalized phosphorous-based end groups of the polymer/oligomer).

The CLFR polymeric material of FIG. 8 may subsequently be used as a Diels-Alder active cross-linker where the two terminal furan groups (on each end of the polymer) act as dienes and may react with polymeric materials functionalized with dienophile functional group(s). For example, a dienophile such as a succinimide-functionalized polymer or a succinic anhydride-functionalized polymer may be used, and the resulting cross-linking reaction can be rendered reversible under specific thermal conditions. The furan groups in the CLFR backbone do not react under standard Diels-Alder reaction conditions as they are deactivated (electron-deficient) due to the flanking carbonyl groups. Thus, only the terminal furan groups react under standard Diels-Alder reaction conditions.

Thus, FIG. 8 illustrates an example of a process of utilizing a furan-containing FR molecule of the present disclosure to form a cross-linkable flame retardant polymeric material. In the example of FIG. 8, the CLFR polymeric material includes two terminal furan groups (on each end of the polymer chain). The terminal furan group represents a diene group that provides a potential cross-linking location for reaction with a dienophile functional group of another polymeric material.

Figure 9:
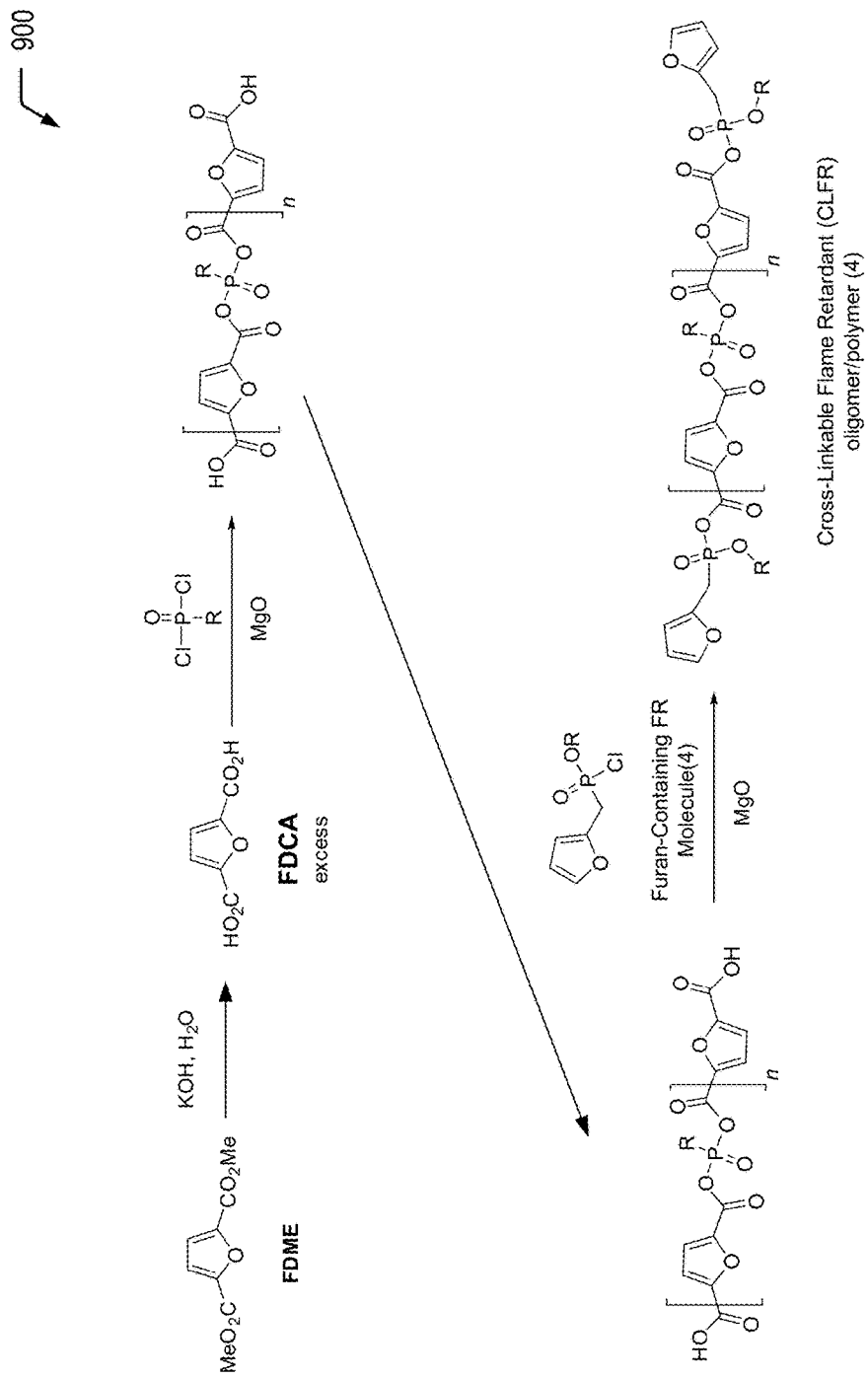
FIG. 9 is a chemical reaction diagram showing a particular embodiment of a process of utilizing the fourth furan-containing flame retardant molecule depicted in FIG. 1 to form a cross-linkable flame retardant material.

Referring to FIG. 9, a chemical reaction diagram 900 illustrates a particular embodiment of a process of utilizing the fourth furan-containing FR molecule depicted in FIG. 1 to form a cross-linkable flame retardant material.

The first chemical reactions depicted at the top of FIG. 9 illustrate that FDME may be used to form a polymeric backbone. In some embodiments, FDME may be produced from renewable resource-derived fructose. The second chemical reaction depicted at the bottom of FIG. 9 illustrates that the fourth furan-containing FR molecule of FIG. 1 may be used to form a CLFR polymeric/oligomeric material with one terminal furan group (on each end of the polymer). The fourth furan-containing FR molecule of FIG. 1 may be bound to the terminal ends of the polymeric backbone via a chemical reaction of the chloride group and a hydroxyl group.

As a prophetic example, CLFR (4) of FIG. 9 may be prepared in a similar fashion to CLFR (1) of FIG. 6 in which the second furan-containing molecule may be substituted for the first furan-containing molecule during the third and final reaction step (addition of furan-functionalized phosphorous-based end groups of the polymer/oligomer).

The CLFR polymeric material of FIG. 9 may subsequently be used as a Diels-Alder active cross-linker where the terminal furan group (on each end of the polymer) acts as a diene and may react with polymeric materials functionalized with dienophile functional group(s). For example, a dienophile such as a succinimide-functionalized polymer or a succinic anhydride-functionalized polymer may be used, and the resulting cross-linking reaction can be rendered reversible under specific thermal conditions. The furan groups in the CLFR backbone do not react under standard Diels-Alder reaction conditions as they are deactivated (electron-deficient) due to the flanking carbonyl groups. Thus, only the terminal furan group reacts under standard Diels-Alder reaction conditions.

Thus, FIG. 9 illustrates an example of a process of utilizing a furan-containing flame retardant molecule of the present disclosure to form a cross-linkable flame retardant material. In the example of FIG. 9, the CLFR polymeric material includes one terminal furan group (on each end of the polymer chain). The terminal furan group represents a diene group that provides a potential cross-linking location for reaction with a dienophile functional group of another polymeric material.

FIG. 10 illustrates that the furan-containing FR molecules of the present disclosure may be utilized to form a cross-linkable flame retardant particle (CLFRP). In some cases, the CLFRP may be blended with a matrix polymer that contains dienophiles such as a succinic anhydride-functionalized polymer. The resulting cross-linking reaction can be rendered reversible under specific thermal conditions. Alternatively, FIG. 11 illustrates that the CLFRP of FIG. 10 (or another CLFRP formed from another furan-containing FR molecule depicted in FIG. 1) may be reacted with a corresponding dienophile-modified particle via a Diels-Alder reaction. The reaction may be rendered reversible under specific thermal conditions.

Referring to FIG. 10, a chemical reaction diagram 1000 shows a particular embodiment of a process of utilizing the first furan-containing FR molecule depicted in FIG. 1 to form a CLFRP. It will be appreciated that the other furan-containing FR molecules depicted in FIG. 1 may also be utilized to form corresponding CLFRPs. Thus, FIG. 10 depicts a non-limiting, illustrative example of a CLFRP that may be formed from one of the furan-containing FR molecules of the present disclosure.

In FIG. 10, a furan-containing FR molecule is chemically reacted with a surface of a hydroxyl-containing particle (e.g., a silica particle surface or any reactive filler that has free hydroxyls). Other examples of hydroxyl-containing particles include glass microbeads, cellulose nanocrystals, cellulose nanofibrils, ZnO or another hydro-containing oxide. In a particular embodiment, a suspension of silica particles may be reacted with furan-containing FR molecules to form a CRFP having diene functionality.

As a prophetic example, a solution or suspension may be prepared of the hydroxyl-functionalized particles, and an excess of triethylamine (or another amine based, such as diisopropyl amine, DBU, or DABCO) in an organic solvent or mixture of organic solvents which be any of the following: toluene, THF, DMF, DMSO, HMPA, NMP, dioxane, ethyl acetate, acetone, DCM, chloroform, chlorobenzene, pyridine, or acetonitrile. The first, second, third, or fourth furan-containing FR molecule may be added dropwise, and the reaction mixture may be stirred at room temperature, heated up to 40-150° C. for 0.5-24.0 hours. The reaction mixture may be cooled to room temperature and subsequently rinsed with 1M HCl, and saturated $NaHCO_3$(aq.), brine, and dried over $MgSO_4$. The solvent may be removed in vacuo, and the crude product purified by any combination of recrystallization, re-precipitation, or chromatography.

In some cases, the CLFRP of FIG. 10 may be blended with a matrix polymer that contains dienophiles such as a succinic anhydride-functionalized polymer. The resulting cross-linking reaction can be rendered reversible under specific thermal conditions. Alternatively, FIG. 11 is a diagram 1100 illustrating that the CLFRP of FIG. 10 may be reacted with a corresponding dienophile-modified particle via a Diels-Alder reaction. The reaction may be rendered reversible under specific thermal conditions.

Figure 12:
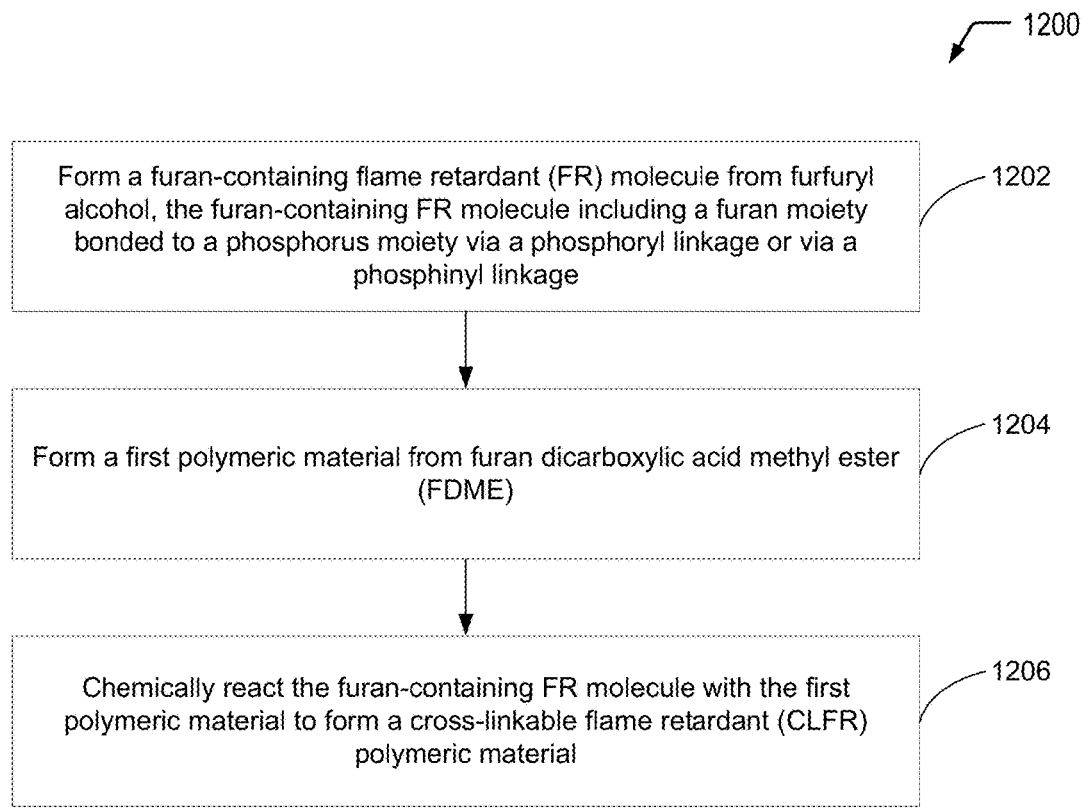
FIG. 12 is a flow diagram showing a particular embodiment of a process of forming a cross-linkable flame retardant polymeric material from a furan-containing flame retardant molecule.

Referring to FIG. 12, a flow diagram illustrates an example of a process 1200 of forming a CLFR polymeric material from a furan-containing flame retardant molecule. It will be appreciated that the operations shown in FIG. 12 are for illustrative purposes only and that the operations may be performed in alternative orders, at alternative times, by a single entity or by multiple entities, or a combination thereof. As an example, one entity may form the furan-containing FR molecule from the furfuryl alcohol (depicted as operation 1202 in FIG. 12), while another entity may form a polymeric backbone from FDME (depicted as operation 1204 in FIG. 12), while yet another entity may chemically react the furan-containing FR molecule with the polymeric backbone formed from FDME to form the CLFR polymeric material (depicted as operation 1206 in FIG. 12).

The process 1200 includes forming a furan-containing FR molecule from furfuryl alcohol, at 1202. The FR furan-containing molecule includes a furan moiety bonded to a phosphorus moiety via a phosphoryl linkage or a phosphinyl linkage. For example, the first FR furan-containing molecule depicted in FIG. 1 (e.g., a difuran-functionalized phosphate material) may be formed from furfuryl alcohol according to the process described herein with respect to FIG. 2. As another example, the second furan-containing FR molecule depicted in FIG. 1 (e.g., a monofuran-functionalized phosphate material) may be formed from furfuryl alcohol according to one of the processes described herein with respect to FIGS. 3A and 3B. As a further example, the third furan-containing FR molecule depicted in FIG. 1 (e.g., a difuran-functionalized phosphine oxide material) may be formed from furfuryl alcohol according to one of the processes described herein with respect to FIGS. 4A and 4B. As yet another example, the fourth furan-containing FR molecule depicted in FIG. 1 (e.g., a monofuran-functionalized phosphonate material) may be formed from furfuryl alcohol according to one of the processes described herein with respect to FIGS. 5A and 5B.

The process 1200 includes forming a first polymeric material from FDME, at 1204. For example, referring to FIGS. 6-9, FDME may be utilized to form a polymeric backbone with terminal carboxylic acid groups for subsequent reaction with the furan-containing FR molecules of the present disclosure. In some cases, FDME may be derived from renewable fructose, thereby increasing renewable content.

The process 1200 includes chemically reacting the furan-containing FR molecule with the polymeric material formed from FDME to form a CLFR polymeric material, at 1206. For example, referring to FIG. 6, the FDME-derived polymeric material may be chemically reacted with the first furan-containing FR molecule of FIG. 1 (a difuran-functionalized phosphate molecule) to form the first CLFR polymeric material (having two terminal furan groups on each end of the polymer). A chemical reaction between the chloride group of the first furan-containing FR molecule and a terminal hydroxyl group may bind the first furan-containing FR molecule to the FDME-derived material. As another example, referring to FIG. 7, the FDME-derived polymeric material may be chemically reacted with the second furan-containing FR molecule of FIG. 1 (a monofuran-functionalized phosphate molecule) to form the second CLFR polymeric material (having one terminal furan group on each end of the polymer). A chemical reaction between the chloride group of the second furan-containing FR molecule and a terminal hydroxyl group may bind the second furan-containing FR molecule to the FDME-derived material. As a further example, referring to FIG. 8, the FDME-derived polymeric material may be chemically reacted with the third furan-containing FR molecule of FIG. 1 (a difuran-functionalized phosphine oxide molecule) to form the third CLFR polymeric material (having two terminal furan groups on each end of the polymer). A chemical reaction between the chloride group of the third furan-containing FR molecule and a terminal hydroxyl group may bind the third furan-containing FR molecule to the FDME-derived material. As yet another example, referring to FIG. 9, the FDME-derived polymeric material may be chemically reacted with the fourth furan-containing FR molecule of FIG. 1 (a mono-furan-functionalized phosphonate molecule) to form the fourth CLFR polymeric material (having one terminal furan group on each end of the polymer). A chemical reaction between the chloride group of the fourth furan-containing FR molecule and a terminal hydroxyl group may bind the fourth furan-containing FR molecule to the FDME-derived material.

Thus, FIG. 12 illustrates an example of a process of utilizing the furan-containing flame retardant molecules of the present disclosure and an FDME-derived material to form a CLFR polymeric material. FIG. 12 illustrates that the CLFR polymeric material may include one or more terminal furan groups on each end of the polymer, providing the ability to vary a degree of subsequent cross-linking (e.g., with another polymeric material, such as another renewable polymeric material or a non-renewable polymeric material).

Figure 13:
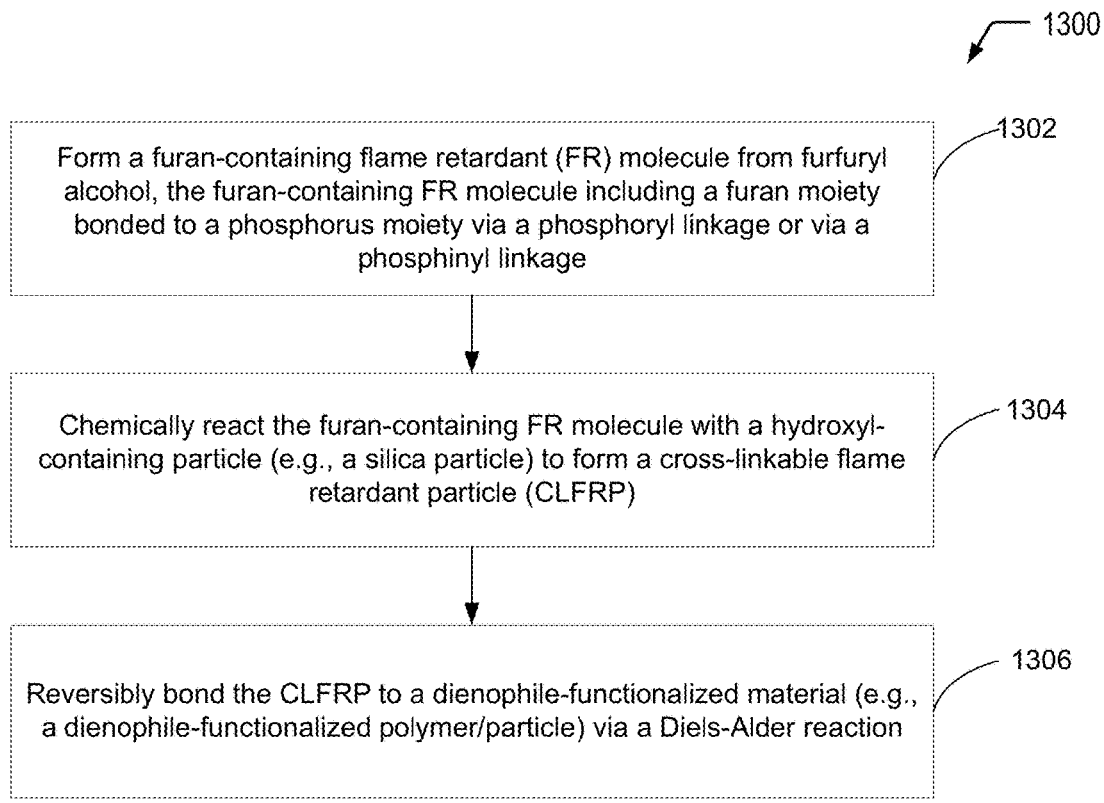
FIG. 13 is a flow diagram showing a particular embodiment of a process of forming a cross-linkable flame retardant particle from a furan-containing flame retardant molecule.

Referring to FIG. 13, a flow diagram illustrates an example of a process 1300 of forming a cross-linkable flame retardant particle (CLFRP) from a furan-containing FR molecule. In the particular embodiment depicted in FIG. 13, the process 1300 further includes reversibly cross-linking the CLFR particle to another material that is functionalized with a dienophile group (e.g., a dienophile-functionalize polymeric material or a dienophile-functionalized particle). It will be appreciated that the operations shown in FIG. 13 are for illustrative purposes only and that the operations may be performed in alternative orders, at alternative times, by a single entity or by multiple entities, or a combination thereof. As an example, one entity may form the furan-containing FR molecule from the furfuryl alcohol (depicted as operation 1302 in FIG. 13), while another entity may utilize the furan-containing FR molecule to form the CLFRP (depicted as operation 1304 in FIG. 13), while yet another entity may reversibly bond the CLFRP to a dienophile-functionalized material via a Diels-Alder reaction (depicted as operation 1306 in FIG. 13).

The process 1300 includes forming a furan-containing FR molecule from furfuryl alcohol, at 1302. The furan-containing FR molecule includes a furan moiety bonded to a phosphorus moiety via a phosphoryl linkage or a phosphinyl linkage. For example, the first furan-containing FR molecule depicted in FIG. 1 (e.g., a difuran-functionalized phosphate material) may formed according to the process described herein with respect to FIG. 2. As another example, the second furan-containing FR molecule depicted in FIG. 1 (e.g., a monofuran-functionalized phosphate material) may be formed according to one of the processes described herein with respect to FIGS. 3A and 3B. As a further example, the third furan-containing FR molecule depicted in FIG. 1 (e.g., a difuran-functionalized phosphine oxide material) may be formed according to one of the processes described herein with respect to FIGS. 4A and 4B. As yet another example, the fourth furan-containing FR molecule depicted in FIG. 1 (e.g., a monofuran-functionalized phosphonate material) may be formed according to one of the processes described herein with respect to FIGS. 5A and 5B.

The process 1300 includes chemically reacting the FR furan-containing molecule with a hydroxyl-containing particle (e.g., a silica particle) to form a CLFRP, at 1304. For example, referring to FIG. 10, the silica particle may be chemically reacted with the first furan-containing FR molecule of FIG. 1 to form the CLFRP. While not shown in the example of FIG. 10, similar chemical reactions may occur between a hydroxyl-containing particle (e.g., a silica particle) and the other furan-containing FR particles depicted in FIG. 1.

The process 1300 further includes reversibly cross-linking the CLFRP to a dienophile-functionalized material via a Diels-Alder reaction, at 1306. For example, referring to FIG. 11, the CLFRP of FIG. 10 may be reversibly bonded to a dienophile-functionalized particle (e.g., a dienophile-functionalized silica particle) via a Diels-Alder reaction. Alternatively, while not shown in the example of FIG. 11, the CLFRP of FIG. 10 may be reversibly bonded to a polymeric material that includes dienophile functional groups.

Thus, FIG. 13 illustrates an example of a process of utilizing the furan-containing FR molecules of the present disclosure to form a CLFR particle. The furan moieties bonded to the CLFRP provide available location(s) for reversible cross-linking with another material that includes dienophile functional groups.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a furan-containing flame retardant molecule from furfuryl alcohol, the process comprising:
   chemically reacting furfuryl alcohol with phosphorus trichloride to form a phosphine oxide intermediate material; and
   utilizing the phosphine oxide intermediate material to form a furan-containing flame retardant molecule having the following chemical structure:

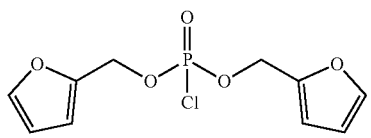 [SMILES: O=P(Cl)(OCc1ccco1)OCc1ccco1]

2. The process of claim 1, wherein utilizing the phosphine oxide intermediate material to form the furan-containing flame retardant molecule includes chemically reacting the phosphine oxide intermediate material with isocyanuric chloride.

3. The process of claim 1, wherein utilizing the phosphine oxide intermediate material to form the furan-containing flame retardant molecule includes chemically reacting the phosphine oxide intermediate material with tert-butyl hypochlorite.

4. A process of forming a furan-containing flame retardant molecule from furfuryl alcohol, the process comprising:
   chemically reacting furfuryl alcohol with thionyl chloride to form a chloromethylfuran intermediate material; and
   utilizing the chloromethylfuran intermediate material to form a furan-containing flame retardant molecule having a chemical structure selected from the group consisting of:

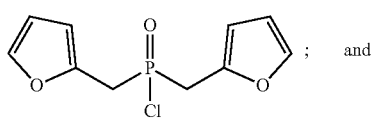 [SMILES: O=P(Cl)(Cc1ccco1)Cc1ccco1] ; and

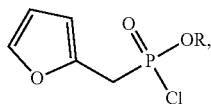

wherein R corresponds to an alkyl group or a phenyl group.

5. The process of claim 4, wherein utilizing the chloromethylfuran intermediate material to form the furan-containing flame retardant molecule includes:
   utilizing the chloromethylfuran intermediate material to form a phosphinic acid intermediate material; and
   chemically reacting the phosphinic acid intermediate material with thionyl chloride to form the furan-containing flame retardant molecule.

6. The process of claim 4, wherein utilizing the chloromethylfuran intermediate material to form the furan-containing flame retardant molecule includes:
   utilizing the chloromethylfuran intermediate material to form a phosphinic ester intermediate material; and
   chemically reacting the phosphinic ester intermediate material with phosphorus pentachloride to form the furan-containing flame retardant molecule.

7. The process of claim 4, wherein utilizing the chloromethylfuran intermediate material to form the furan-containing flame retardant molecule includes:
   utilizing the chloromethylfuran intermediate material to form a phosphinyl ester intermediate material; and
   chemically reacting the phosphinyl ester intermediate material with phosphorus pentachloride to form the furan-containing flame retardant molecule.

8. The process of claim 4, wherein utilizing the chloromethylfuran intermediate material to form the furan-containing flame retardant molecule includes:
   utilizing the chloromethylfuran intermediate material to form a phosphinyl ester intermediate material; and
   chemically reacting the phosphinyl ester intermediate material with thionyl chloride to form the furan-containing flame retardant molecule.

9. The process of claim 4, wherein the alkyl group includes an ethyl group, a methyl group, a propyl group, or an isopropyl group.

10. A process of forming a furan-containing flame retardant molecule from furfuryl alcohol, the process comprising:
    chemically reacting furfuryl alcohol with a dichlorophosphate material to form a furan-containing flame retardant molecule having the following chemical structure:

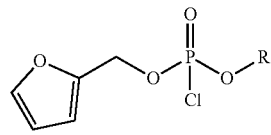

wherein R corresponds to an alkyl group or a phenyl group.

11. The process of claim 10, wherein the alkyl group includes an ethyl group, a methyl group, a propyl group, or an isopropyl group.

* * * * *